(12) United States Patent
Maschat et al.

(10) Patent No.: US 8,987,211 B2
(45) Date of Patent: Mar. 24, 2015

(54) THERAPEUTIC PEPTIDES AND USE THEREOF AGAINST HUNTINGTON'S DISEASE

(75) Inventors: Florence Maschat, Boisseron (FR); Marie-Laure Parmentier, Montpellier (FR); Nathalie Bonneaud, Montpellier (FR); Yoan Arribat, Montpellier (FR)

(73) Assignees: Centre National de la Recherche Scientifique (CNRS), Paris (FR); Institut National de la Sante et de la Recherche Medicale (INSERM), Paris (FR); Universite Montpellier 2 Sciences et Techniques, Montpellier (FR)

( * ) Notice: Subject to any disclaimer, the term of this patent is extended or adjusted under 35 U.S.C. 154(b) by 0 days.

(21) Appl. No.: 14/111,285

(22) PCT Filed: Apr. 12, 2012

(86) PCT No.: PCT/FR2012/050809
§ 371 (c)(1),
(2), (4) Date: Dec. 24, 2013

(87) PCT Pub. No.: WO2012/140376
PCT Pub. Date: Oct. 18, 2012

(65) Prior Publication Data
US 2014/0121167 A1    May 1, 2014

(30) Foreign Application Priority Data
Apr. 12, 2011    (FR) .................................... 11 53193

(51) Int. Cl.
| A61K 38/16 | (2006.01) |
| A61K 38/00 | (2006.01) |
| A61K 48/00 | (2006.01) |
| A61K 38/10 | (2006.01) |
| C12N 15/00 | (2006.01) |
| C07K 5/00 | (2006.01) |
| C07H 21/04 | (2006.01) |
| C12N 15/62 | (2006.01) |

(Continued)

(52) U.S. Cl.
CPC ................ *C12N 15/62* (2013.01); *C07K 14/47* (2013.01); *C07K 4/12* (2013.01); *C07K 2319/00* (2013.01); *A61K 38/00* (2013.01); *C07K 2319/41* (2013.01); *C07K 2319/60* (2013.01)
USPC ....... 514/21.2; 435/320.1; 514/17.7; 514/1.1; 514/44 R; 514/21.4; 530/326; 530/327; 536/23.4

(58) Field of Classification Search
None
See application file for complete search history.

(56) References Cited

FOREIGN PATENT DOCUMENTS
WO    01/68678 A2    9/2001
WO    WO 2004/103159    * 12/2004

(Continued)

OTHER PUBLICATIONS

Davies and Sanchez 2005 "FKBP52" IJBCB 37:42-47.*

(Continued)

*Primary Examiner* — Gregory S Emch
*Assistant Examiner* — Adam M Weidner
(74) *Attorney, Agent, or Firm* — Young & Thompson

(57) ABSTRACT

Fusion proteins that contain the fusion of (i) a peptide of less than 100 amino acids comprising a first amino acid sequence comprising AASSG (SEQ ID NO: 1) and a second amino acid sequence comprising XAGXDXXTEXPXS (SEQ ID NO: 2), wherein X designates any amino acid, and (ii) a protein transduction domain (PTD) are provided, along with pharmaceutical compositions containing the fusion protein. The proteins can be used to treat Huntington's disease.

21 Claims, 9 Drawing Sheets

(51) Int. Cl.
*C07K 14/47* (2006.01)
*C07K 4/12* (2006.01)

(56) References Cited

FOREIGN PATENT DOCUMENTS

WO 2006/078648 A2 7/2006
WO 2010/017408 A1 2/2010

OTHER PUBLICATIONS

Popiel et al.: "Protein transduction domain-mediated delivery of QBP1 suppresses polyglutamine-induced neurodegeneration in vivo.", Molecular Therapy. The Journal of the American Society of Gene Therapy Feb. 2007 LNKD-PUBMED:17235308, vol. 15, No. 2, Feb. 2007, pp. 303-309, XP002669683, ISSN: 1525-0016 the whole document.

Wada S et al.: "Rationale for Antiangiogenic Cancer Therapy with Vaccination Using Epitope Peptides Derived from Human Vascular Endothelial Growth Factor Receptor 2", Cancer Research, American Association for Cancer Research, US, vol. 65, No. II, Jun. 1, 2005, pp. 4939-4946, XP002348368, ISSN: 0008-5472, DOI:10.1158/0008-5472.CAN-04-3759 peptide No. 36; p. 4940; table.

Mugat Bruno et al.: "Protective role of Engrailed in a *Drosophilia* model of Huntington's disease", Human Molecular Genetics, vol. 17, No. 22, Aug. 20, 2008, pp. 3601-3616, XP002669684.

Database Geneseq [Online] Apr. 29, 2010, "Huntingtin proteolysis fragment protein sequence, SEQ ID No. 1.", XP002669682, retrieved from EBI accession No. GSP:AXW36976 Database accession No. AXW36976 the whole document & WO 2010/017408 A1 (Buck Inst for Age Res [US]; Univ California [US]; Ellerby Lisa M [US];) Feb. 11, 2010 figure 11.

Nagai Y et al.: "Inhibition of Polyglutamine Protein Aggregation and Cell Death by Novel Peptides Identified by Phage Display Screening", Journal of Biological Chemistry, The American Society of Biological Chemists, Inc, US, vol. 275, No. 14, Apr. 7, 2000, pp. 10437-10442, XP002938480, ISSN: 0021-9258, DOI: 10.1074/JBC.275.14.10437 the whole document.

International Search Report, dated Jul. 4, 2012, from corresponding PCT application.

* cited by examiner

A - dHtt (1-620aa)
MDKSRSSAYDKFVGFVEQLRNTECSQKQKITCFQQIAECIMSPSLAGHIN
YAAHCGTATNVLLLFCEDVDSVVRMSAEENLNKILRSLEKTRVSRILMDL
YGEIKRNGNQRSLRICLNLFSYYAPQIKEKHIKWYAVRLLQCMTTISQRK
ETLLQETLCDFVKHFSRHIQQGLSDSESCKLFETFLDQISSDCAVKRRCS
AQNCMSLIENARNRSLMARHGVNKVMELLLTDQQANSVLGALGLLRLLLP
QLIRGYPGDSHEDSESLAGKKQQQQQTTTSDCRQIIEIYDYCLHLLSTQH
TANHAIINATLEVINGILQAVDAASDGQCSQSLGQSLRQLLCNQQLQHNE
YLRRRKSLKNQIFQLKNYEVATSQHQLEDEDENEDVDELVVGATAMQMKK
NSNAKLQQAKCREQQQHQHQQQLEVDNSSLGINAGEDAPTEAPSSVADEG
GEPESTKLRCHIRNAARSISECVASDEDKQGQGHRQQRDEDGVVVAEDDD
DDDDDDDDDDMELLSAECDDFTTLSQLNEQQQALSAALKLPTTTAASSG
GAATSQDDKLIDVDADVGGLPKPQHQSSLQNLLAGSDDKSQHLSDIDNES
FNSIDFDAEITIAGSKEQQQ

B - hHtt (1-548aa)
MATLEKLMKAFESLKSFQQQQQQQQQQQQQQQQQQQQQPPPPPPPPPPPQ
LPQPPPQAQPLLPQPQPPPPPPPPPGPAVAEEPLHRPKKELSATKKDRV
NHCLTICENIVAQSVRNSPEFQKLLGIAMELFLLCSDDAESDVRMVADEC
LNKVIKALMDSNLPRLQLELYKEIKKNGAPRSLRAALWRFAELAHLVRPQ
KCRPYLVNLLPCLTRTSKRPEESVQETLAAAVPKIMASFGNFANDNEIKV
LLKAFIANLKSSSPTIRRTAAGSAVSICQHSRRTQYFYSWLLNVLLGLLV
PVEDEHSTLLILGVLLTLRYLVPLLQQQVKDTSLKGSFGVTRKEMEVSPS
AEQLVQVYELTLHHTQHQDHNVVTGALELLQQLFRTPPPELLQTLTAVGG
IGQLTAAKEESGGRSRSGSIVELIAGGGSSCSPVLSRKQKGKVLLGEEEA
LEDDSESRSDVSSSALTASVKDEISGELAASSGVSTPGSAGHDIITEQPRS
QHTLQADSVDLASCDLTSSATDGDEEDILSHSSSQVSAVPSDPAMDLND
GTQASSPISDSSQTTTEGPD

Fig. 1

A – Sequence Peptide   Pep4 – SEQ ID N°5

QQLFRTPPPELLQTLTAVGGIGQLTAAKEESGGRSRSGSIVELIAGGGSSCSPVL
SRKQKGKVLLGEEEALEDDSESRSDVSSSALTASVKDEISGEL▓▓▓▓VSTPGS
AGHDIITEQPRSQHTLQADSVDLASCDLTSSATDGDEEDILSHSSSQVSAVPSD
PAM

B – Sequence Nucleotide   – SEQ ID N°8
CAGCAGCTCTTCAGAACGCCTCCACCCGAGCTTCTGCAAACCCTGACTGC
AGTCGGGGGCATTGGGCAGCTCACCGCTGCTAAGGAGGAGTCTGGTGGCC
GAAGCCGTAGTGGGAGTATTGTGGAACTTATAGCTGGAGGGGGTTCCTCA
TGCAGCCCTGTCCTTTCAAGAAAACAAAAAGGCAAAGTGCTCTTAGGAGA
AGAAGAAGCCTTGGAGGATGACTCTGAATCGAGATCGGATGTCAGCAGCT
CTGCCTTAACAGCCTCAGTGAAGGATGAGATCAGTGGAGAGCTGGCTGCT
TCTTCAGGGGTTTCCACTCCAGGGTCAGCAGGTCATGACATCATCACAGA
ACAGCCACGGTCACAGCACACACTGCAGGCGGACTCAGTGGATCTGGCCA
GCTGTGACTTGACAAGCTCTGCCACTGATGGGGATGAGGAGGATATCTTG
AGCCACAGCTCCAGCCAGGTCAGCGCCGTCCATCTGACCCTGCCATG C – Sequence Peptide   Pep42 – SEQ ID N°4
▓▓▓▓VSTPGSAGHDIITEQPRS D – Sequence Nucleotide   – SEQ ID N°7
GCTGCTTCTTCAGGGGTTTCCACTCCAGGGTCAGCAGGTCATGACATCAT
CACAGAACAGCCACGGTCA

Fig. 2

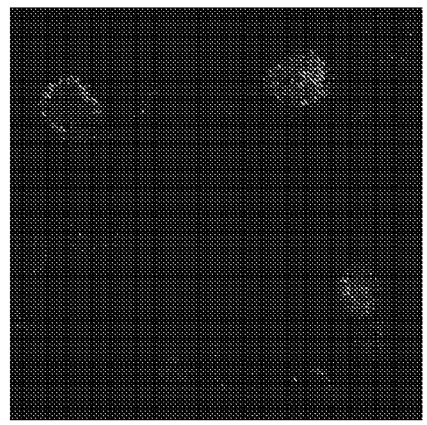
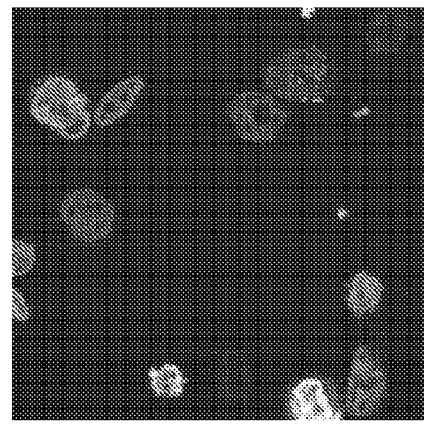
Fig. 7a                    Fig. 7b
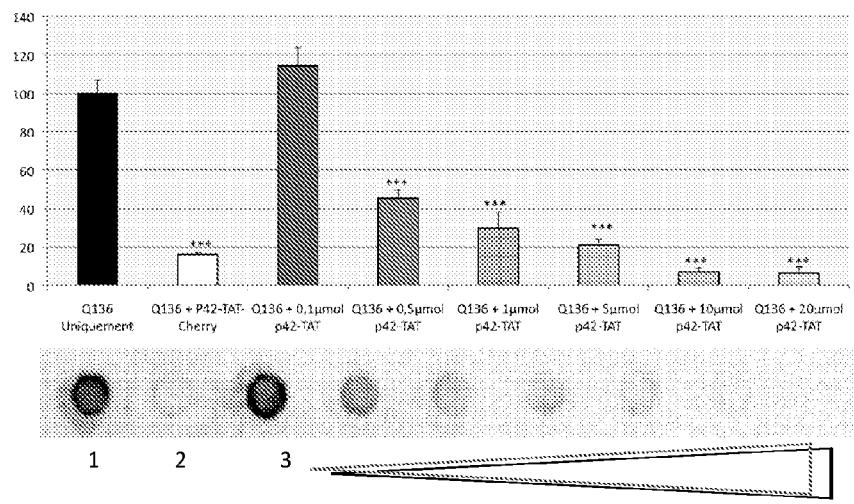
Fig. 7c

THERAPEUTIC PEPTIDES AND USE THEREOF AGAINST HUNTINGTON'S DISEASE

SEQUENCE LISTING

An attached Substitute Sequence Listing (i. Name: SEQCRF_0611-1007, ii. Date of Creation: Dec. 20, 2013, and iii. Size: 15.5 KB) is based on the Sequence Listing filed with U.S. application Ser. No. 14/111,285. The entire contents of each of the above-identified Sequence Listings are hereby incorporated by reference.

FIELD OF THE INVENTION

This invention relates to novel therapeutic compounds for use against Huntington's disease. These therapeutic compounds contain, or code for, a particular peptide sequence.

BACKGROUND OF THE INVENTION

Huntington's disease (HD) is a rare neurodegenerative genetic disorder that affects motor and cognitive functions, ultimately leading to dementia. In addition, although the disease is not itself fatal, it induces health complications (pneumonia, cardiac disorders) reducing the life expectancy of the person affected to about twenty years following the onset of symptoms.

It has been demonstrated that this disease is caused by a unique genetic mutation of the gene coding for the human Huntingtin protein (hHtt). This leads to synthesis of an abnormal protein, inducing neuronal disorders in the brain of the person affected by the disease.

FIG. 3 is a diagram of the gene of the human form of Huntingtin (hHtt). This gene contains 3144 amino acids. The N-terminal (N-term) fragment of this gene is shown in more detail. This N-term fragment contains 548 amino acids (including a domain rich in proline amino acids) as well as a polyglutamine (PolyQ) domain, of variable size, ranging from 0Q to 35Q for a normal protein. This polyQ domain corresponds to a sequence composed exclusively of glutamine amino acids (whose abbreviation to a corresponding letter is "Q").

More specifically, in Huntington's disease, the abnormal protein is characterised by abnormal expansion of the polyQ domain contained in the N-terminal fragment of the hHtt protein.

When this domain exceeds 35Q, the polyQ-hHtt protein forms aggregates leading to degeneration of neurons in the striatum (a nervous structure responsible for motor function). Several studies have also identified an influence of the normal function of the Huntingtin protein in the disease.

To date, however, there is no effective treatment against this disease.

One treatment approach currently considered consists in fighting against aggregation of the polyQ domains in the protein, responsible for the disease.

A previous study (Mugat et al., Human Molecular Genetics, 2008) demonstrated a protective role of wild-type hHtt and its Drosophila homolog dHtt concerning aggregation of the polyQ-hHtt proteins. It was in fact possible to rescue the phenotypes induced by the polyQ-hHtt mutant protein with the 548 amino acid (aa) N-terminus (N-ter) fragment of hHtt or with the 620aa N-ter fragment of the Drosophila homolog of Htt (dHtt). These sequences are shown on FIGS. 1B and 1A respectively. FIG. 1B shows on the first line the series of glutamine amino acids (21Q in total) of this normal hHtt protein.

However, use of a protein of 548 and/or 620 amino acids could not reasonably be considered in the context of a genetic therapy. Indeed, in view of the numerous functions carried out by the huntingtin protein and in particular by its N-terminal end, these proteins would also be likely to carry out other functions whose type is not controlled.

The invention therefore relates to particularly targeted novel compounds that can be used as a drug to treat Huntington's disease.

SUMMARY OF THE INVENTION

According to a first aspect of the invention, it relates to an isolated peptide of size less than or equal to 200 amino acids, preferably 100 and containing:
  a first sequence having at least 80% identity with sequence AASSG (SEQ ID NO: 1), and/or
  a second sequence having at least 80% identity with sequence XAGXDXXTEXPXS (SEQ ID NO: 2), where X designates any amino acid.

"Identity percentage" refers to the percentage of identical residues between two sequences.

Preferably, the first and second sequences of the peptide according to the invention have at least 90% identity, more preferably at least 95%.

These sequences have been isolated amongst the N-ter fragments of 548 and 620aa of the hHtt and dHtt proteins, having a protective effect on the aggregation of polyQ-hHtt proteins.

Advantageously, the isolated peptide according to the invention will contain both the first sequence and the second sequence.

200 amino acids is an acceptable size in peptide therapy. However, a smaller size will be preferred in order to optimise the peptide selectivity. Advantageously, the size of the peptide will be less than or equal to 100 amino acids, preferably less than or equal to 80, more preferably less than or equal to 50, and even more preferably less than or equal to 40, 39, 38, 37 or 36.

Peptides are particularly advantageous for use in the context of peptide therapy since they can be both highly efficient and selective, if very specific. In addition, they exhibit low toxicity.

DETAILED DESCRIPTION OF THE INVENTION

According to a first embodiment, the second sequence has the following sequence: SAGHDIITEQPRS (SEQ ID NO: 3). More particularly, the peptide contains a sequence having at least 80% identity with sequence AASSGVSTPGSAGHDIITEQPRS (SEQ ID NO: 4) or sequence QQLFRTPPPELLQTLTAVGGIGQLTAAKEESGGRSRSGSIVELIAGGGSSCSPVLSRKQKGKVLLGEEEALEDDSESRSDVSSSALTASVKDEISGELAAS SGVSTPGSAGHDIITEQPRSQHTLQADSVDLASCDLTSSATDGDEEDILSHSSS QVSAVPSDPAM (SEQ ID NO: 5). These sequences have been called respectively pep42 and pep4, as shown on FIG. 2. This figure shows that pep4 and pep42 include the first and second sequences (indicated by an opaque background).

Pep4 then pep42 have been isolated from the 548 aa sequence including the N-ter fragment of the wild-type hHtt protein. Indeed, as shown on FIG. 4, the 548 aa sequence including the N-ter fragment of the wild-type hHtt protein has been divided into 4 subsequences designated respectively pep1, pep2, pep3 and pep4. Unexpectedly, it was subsequence pep4 which proved to be active (see example 1). Consequently, subsequence pep4 was then itself divided into 3 subfragments designated pep41, pep42 and pep43, to demonstrate the activity of a 23 aa sequence, pep42 (see example 2).

Pep4 and pep42 proved capable of rescuing the formation of aggregates in human cells, but also in an entire organism in the non-neuronal cells (such as the salivary glands in the fly) or in larva motor neurons. In the following examples, it was also demonstrated that pep42 is capable of rescuing the physiological behaviours affected by polyQ-hHtt, such as the vesicular axonal transport, larval locomotion or viability and survival of adult flies. Lastly, it was demonstrated that this peptide, lying within a region rich in proteolysis sites, interacts with the N-terminal end of Htt, thereby preventing aggregation of polyQ-hHtt.

More precisely, it has recently been identified that Pep42 interferes with the first step of aggregation (namely nucleation) through an interaction with the N17 region (the first 17 aa). This suggests that Pep42 targets the polyQ-hHtt protein directly, which will have an effect on aggregation and on the resulting phenotypes. These data highlight the therapeutic potential of Pep42 which combines: i) a direct action on the polyQ-hHtt protein, therefore upstream from any other deleterious action; ii) high specificity since the sequences involved are specific regions of Htt; iii) low toxicity since the action of Pep42 involves endogenous domains normally present in the organism; iv) the advantages of peptide technologies for therapeutic purposes.

"Rescue" therefore means that the peptides according to the invention are capable of eliminating the symptoms and/or the harmful effects associated with the disease by preserving and/or restoring the normal physiological functions.

Preferably, the sequences of the peptide according to the invention have at least 90% identity, more preferably at least 95%.

According to a second embodiment, the second sequence has the following sequence: NAGEDAPTEAPSS (SEQ ID NO: 6). This sequence corresponds to that identified in the 620aa N-ter fragment of the wild-type dHtt protein.

Irrespective of the embodiment implemented, the peptide according to the invention will advantageously be incorporated in a fusion protein, to improve penetration by the peptide according to the invention in the cytoplasm of a cell. The invention therefore also relates to a fusion protein containing a peptide according to the invention and a Protein Transduction Domain (PTD). Preferably, the PTD is chosen amongst the group formed by the Transacting Activator of Transcription (TAT) peptide (SEQ ID NO: 11: YGRKKRRQRRR), the Penetratin™-1 peptide (16-amino acid peptide (SEQ ID NO: 12: RQIKIWFQNRRMKWKK) corresponding to the third helix of the Antennapedia homeodomain) and its derivatives and the active peptide of the Engrailed homeodomain.

During synthesis of the Pep42-TAT fusion peptide (SEQ ID NO: 13: AASSGVSTPGSAGHDIITEQPRSG-GYGRKKRRQRRR), according to the usual techniques, 2 amino acids (Glycine) were inserted between the Pep 42 sequence and the TAT sequence, to obtain greater flexibility between the two domains. This peptide is also part of the invention.

The peptides are synthesised in solid phase, via the Fmoc strategy. They are then analysed by mass spectrometry (ESI) to precisely determine the molecular mass of the peptide synthesised. Absence of deletion or double-coupling peptides can be confirmed by comparing the theoretical mass and experimental mass data. The purity of the peptides synthesised is determined by HPLC. The peptides thus controlled and validated are then lyophilised.

In addition, since peptides and proteins are sensitive to proteolytic enzymes, they are easily degraded. It is therefore strongly recommended to chemically modify the ends of the peptides and proteins according to the invention in order to protect them. Such chemical modifications can be chosen amongst acetylations and amidations.

Similarly, the peptides and proteins can be stabilised by the insertion of non-natural amino acids, for example aminohexanoic acid. In the case of a TAT fusion protein, these non-natural amino acids can be inserted in the TAT arginine-rich domain.

According to a second aspect of the invention, the invention relates to a polynucleotide coding for a peptide or a protein described above. In particular, the polynucleotide is chosen amongst the polynucleotides containing a sequence having at least 80% identity with the following sequences:

```
                                              (SEQ ID NO: 7)
GCTGCTTCTTCAGGGGTTTCCACTCCAGGGTCAGCAGGTCATGAC

ATCATCACAGAACAGCCACGGTCA (SEQ ID NO: 8)
CAGCAGCTCTTCAGAACGCCTCCACCCGAGCTTCTGCAAACCCTG

ACTGCAGTCGGGGGCATTGGGCAGCTCACCGCTGCTAAGGAGGA

GTCTGGTGGCCGAAGCCGTAGTGGGAGTATTGTGGAACTTATAGCT

GGAGGGGGTTCCTCATGCAGCCCTGTCCTTTCAAGAAAACAAAAA

GGCAAAGTGCTCTTAGGAGAAGAAGAAGCCTTGGAGGATGACTC

TGAATCGAGATCGGATGTCAGCAGCTCTGCCTTAACAGCCTCAGT

GAAGGATGAGATCAGTGGAGAGCTGGCTGCTTCTTCAGGGGTTTC

CACTCCAGGGTCAGCAGGTCATGACATCATCACAGAACAGCCACG

GTCACAGCACACACTGCAGGCGGACTCAGTGGATCTGGCCAGCTG

TGACTTGACAAGCTCTGCCACTGATGGGGATGAGGAGGATATCTT

GAGCCACAGCTCCAGCCAGGTCAGCGCCGTCCCATCTGACCCTGC

CATG
```

Nucleotide sequences SEQ ID NO: 7 and SEQ ID NO: 8 code respectively for the peptides of sequences SEQ ID NO: 4 and SEQ ID NO: 5.

Preferably, the sequences of the polynucleotides according to the invention have at least 90% identity, more preferably at least 95% identity with sequence SEQ ID NO: 7 or SEQ ID NO: 8.

The invention also relates to an expression vector containing a polynucleotide according to the invention. Advantageously, the vector is virus type, preferably lentivirus type. Lentivirus type vectors can transfect numerous cell types and remarkably favour internalisation in the cell and delivery of the polynucleotide. In some cases, they can also be used to obtain durable incorporation of the polynucleotide into the host cell genome.

The invention also relates to a host cell containing an expression vector according to the invention.

The peptides according to the invention can therefore be used to prevent the formation of aggregates induced by the PolyQ-hHtt abnormal proteins of Huntington's disease.

The peptides, proteins, polynucleotides and vectors according to the invention can therefore be advantageously used to manufacture a drug, in particular a drug to treat Huntington's disease.

The invention also relates to a pharmaceutical composition containing an efficient quantity of a peptide, a protein, a polynucleotide or a vector according to the invention, with a pharmaceutically acceptable carrier.

Advantageously, the pharmaceutical composition according to the invention also contains a second compound chosen amongst the group formed by the peptides directed against polyQ, such as QBP1 (Polyglutamine-Binding Peptide 1) and the compounds active against Huntington's disease. Compounds active against Huntington's disease include the single-chain antibodies (intrabodies) directed against Huntington's disease.

Lastly, the invention relates to a therapeutic treatment method including administration of an efficient quantity of a peptide, a protein, a polynucleotide or a vector according to the invention to a patient affected by Huntington's disease.

BRIEF DESCRIPTION OF THE FIGURES

The invention will be better understood from the following description, given solely by way of example and by referring to the drawings wherein:

FIG. 1 shows the N-terminal portions of sequences of Drosophila (A) and human (B) Huntingtin proteins, FIG. 2 shows sequences of Pep4 (A) and Pep42 (C) peptides and their respective nucleotide sequence (B, D), FIG. 7 illustrates diffusion and activity of the Pep42-TAT fusion peptide in a culture of HeLa cells and, FIG. 8 illustrates diffusion of the Pep42-TAT fusion peptide in the mouse brain and its stability at 24 hours.

EXAMPLE 1

Identification of Peptides Inhibiting polyQ-hHtt Aggregation

Figure 3:
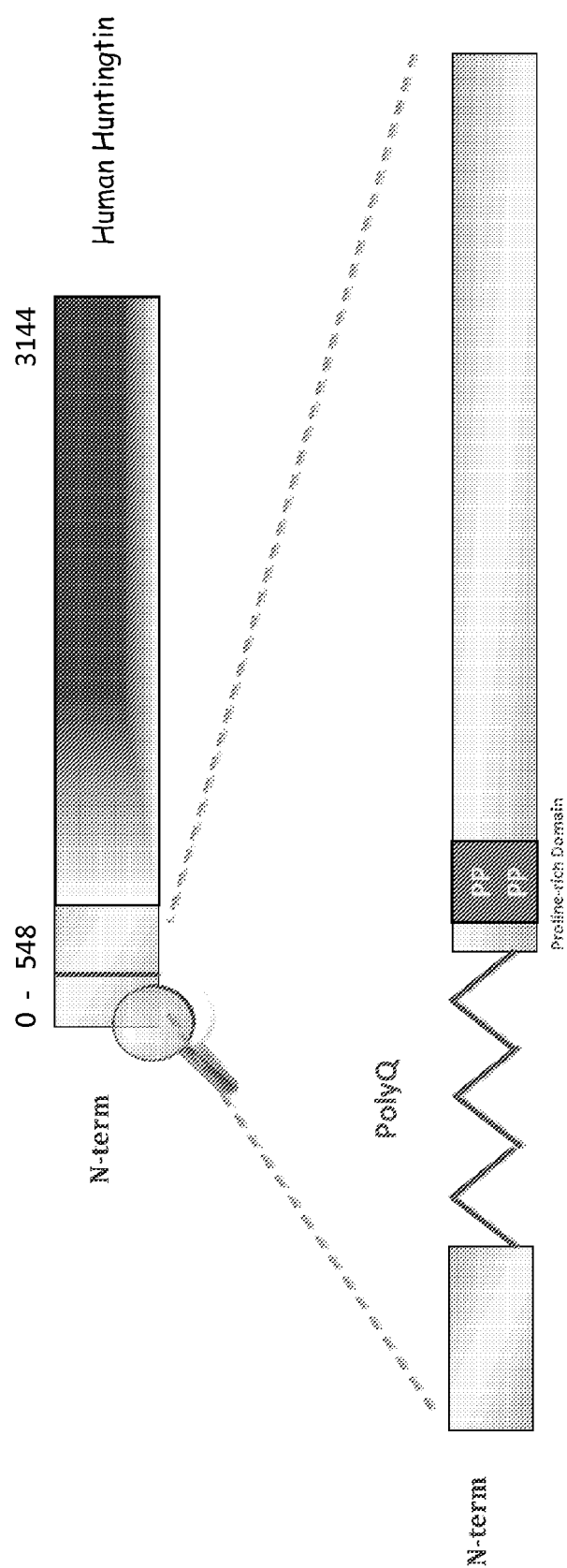
FIG. 3 is a diagram of the human Huntingtin (hHtt) protein showing the N-terminal fragment.
Figure 4:
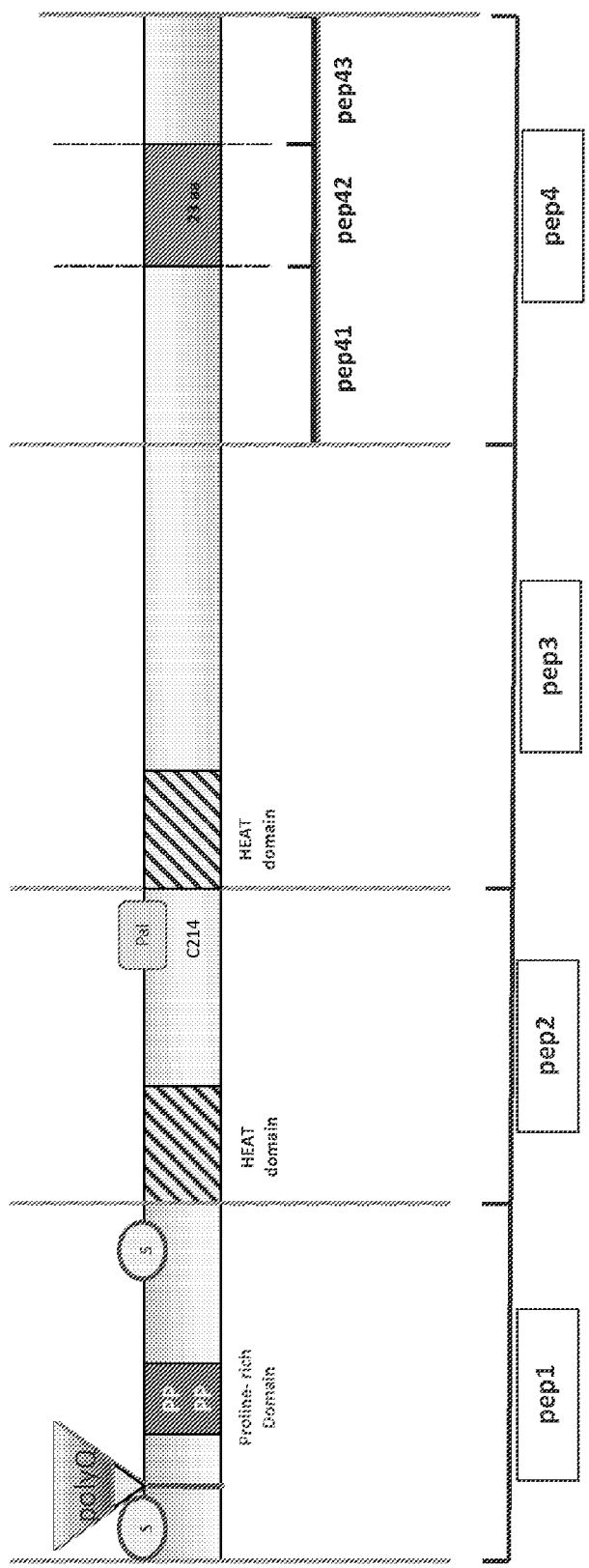
FIG. 4 is a diagram of the breakdown of a 548aa sequence containing the N-terminal fragment shown in FIG. 3, the breakdown corresponding to the various subsequences studied.
Figure 5:
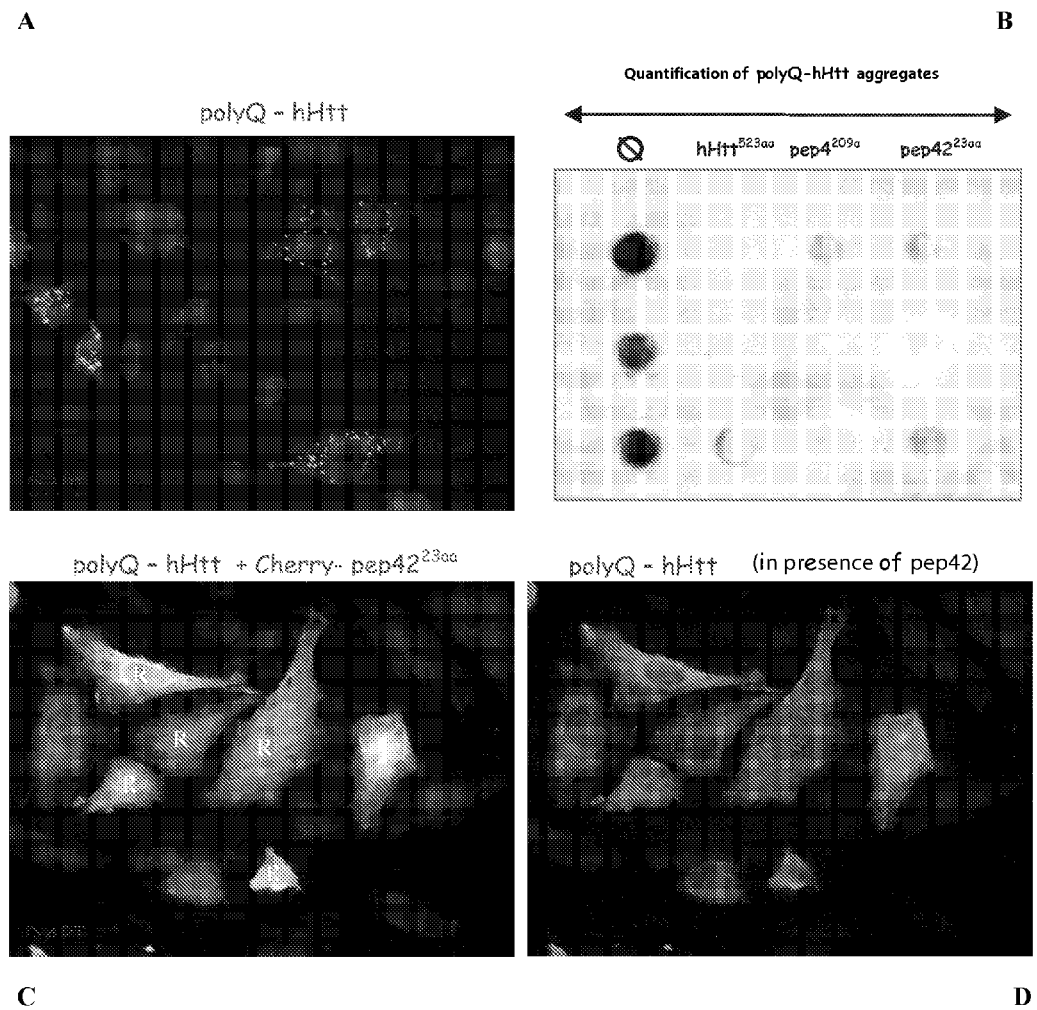
FIG. 5 illustrates the protective effect of the Pep42 peptide on HeLa cells expressing the PolyQ-hHtt protein.

Various peptides contained in the 548aa of the human Huntingtin N-terminal fragment have been cloned by Gateway in expression vectors in pcDNA type cultured HeLa cells. Each peptide was tagged either by Myc or by Cherry at its N-terminal end. These various peptides were tested by cotransfection in HeLa cells in the presence of a pcDNA vector expressing a GFP-polyQ-hHtt protein (see FIG. 5). In these experiments, the polyQ-hHtt protein tested corresponded to an hHtt protein covering 171 aa and containing an extended polyQ with a GFP tag at its N-ter end (GFP-hHtt$^{171aa}$-136Q). The HeLa cells were cultured in 6-well boxes and transfected by 1.5 µg of total DNA, using JetPei (Qbiogene) reagent. Equivalent quantities of expression vectors (polyQ protein and peptides) are used for the cotransfections. When necessary, pBluescript is used to balance the quantity of DNA. Aggregation of GFP-hHtt$^{171aa}$-136Q is visualised by immunodetection with an anti-GFP antibody (see FIG. 5). This protein forms cytoplasmic aggregates (see FIG. 5A). In the presence of pep42, indicated in red on FIG. 5C (symbolised by the letter R), the GFP-hHtt$^{171aa}$-136Q protein no longer forms aggregates as can be seen on FIGS. 5C and 5D compared with FIG. 5A. This analysis was used to identify an inhibiting effect of polyQ-hHtt aggregation by pep4 (covering 166aa between the 382 and 548 amino acids, see FIG. 2A) and by the 23aa peptide (pep42) contained in pep4. This result is confirmed by quantification, as shown in example 3 below.

EXAMPLE 2

Inhibiting Properties of pep42 on polyQ-hHtt Aggregation in the Drosophila

The pep4 and pep42 peptides identified as inhibitors of polyQ-hHtt aggregation in HeLa cells were cloned using the Gateway technique in Drosophila pUASt expression vectors, allowing the expression of N-terminal 6Myc- or GFP-tagged peptides.

Transgenic flies expressing these peptides were constructed by injecting vectors in Drosophila embryos. The UAS/Gal4 system (Brand and Perrimon, Development 1993) was used to express these peptides at specific times and in specific tissues, in the presence of an HA- (hemagglutinin) tagged UAS-polyQ-hHtt vector.

The MS1096-Gal4 driver was used to express the HA-hHtt$^{171aa}$-136Q protein (detected by an anti-HA antibody) in the salivary glands, in the absence or presence of the GFP-pep42 peptide. In the presence of the GFP-pep42 peptide, detected by an anti-GFP, the polyQ-hHtt protein loses the ability to aggregate. Salivary glands from dissected third instar larvae were immunolabelled. The glands are fixed for 20 minutes in PBS with 3.7% paraformaldehyde (PFA) and 0.1% Triton then washed in PBS/0.1% Triton. The glands were incubated with the antibodies (anti-HA, then Cy3 conjugate antibody) with 1% BSA. These immunolabels demonstrated the absence of aggregates in the presence of pep4 or pep42.

EXAMPLE 3

Quantification of Aggregates by Filtration a) Using HeLa Cells.

Protein extracts were obtained according to (Sittler et al., Mol Cell. 1998) with the following modifications: after transfection, the cell pellets are treated with DNase and resuspended in 150 µl 1% SDS and 50 mM DTT in PBS. The samples are boiled for 5 minutes. Two 150 µL aliquots corresponding to independent experiments were filtered together and each point was reproduced 3 times.

b) Using Salivary Glands.

The glands from 3 third instar larvae were dissected and crushed in 30 µL of 2% SDS and 50 mM DTT, then denatured for 7 minutes at 98° C. The samples are then diluted in 200 µL of 0.1% SDS before filtration. For each genotype, the samples were duplicated.

The samples were filtered on a cellulose acetate membrane (0.2 µM, Schleicher and Schuell) using a Biorad Dot-blot apparatus. The membranes were then subjected to immunodetection with an antibody, either anti-GFP polyclonal for the HeLa cells (Invitrogen, 1:5000) or anti-HA polyclonal for the salivary glands (SC805, Santa-Cruz, 1:200) in order to visualise the aggregates The aggregates are then detected using a secondary anti-rabbit antibody coupled with HRP (horseradish peroxidase, Jackson 1:50 000). The immunoreagent spots are detected with an electrochemiluminescent substrate (ECL, Roche) and the quantifications carried out using Image J (see FIG. 5B).

EXAMPLE 4

Inhibiting Properties of pep42 on Eye Toxicity

Figure 6:
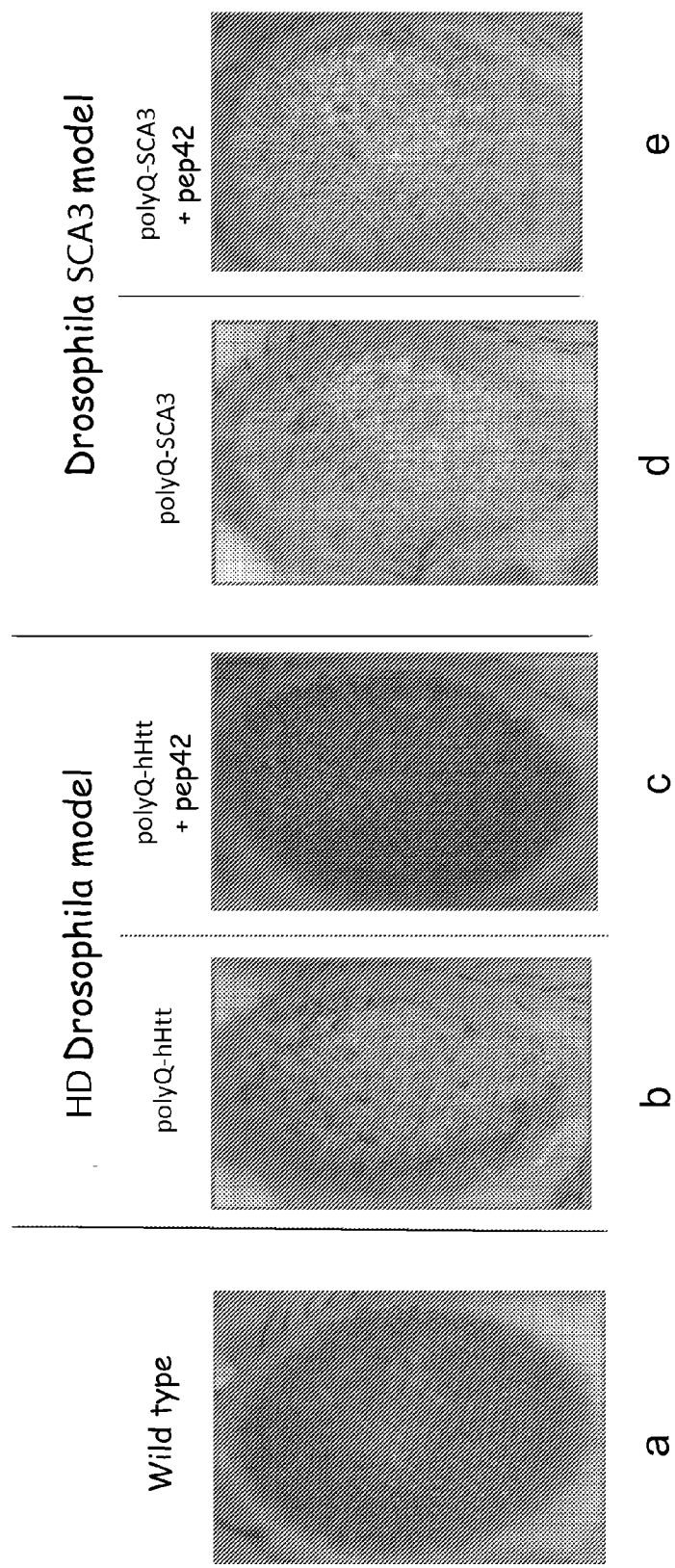
FIG. 6 illustrates the protective effect of the Pep42 peptide on the phenotype responsible for depigmentation and degeneration of drosophila eyes expressing the polyQ-hHtt peptide.

The eye depigmentation and degeneration phenotypes are analysed in 10-day old females expressing either UAS-hHtt$^{67aa}$-98Q or UAS-hHtt$^{548aa}$-128Q controlled by the gmr-Gal4 driver, after transfer at 29° C. from the embryogenesis stage (see FIG. 6b, to be compared with the wild flies shown on FIG. 6a). Flies expressing other genes involved in polyQ diseases (UAS-SCA1-polyQ or UAS-SCA3-polyQ) were also analysed (FIG. 6d). In all cases, the flies exhibit significant degeneration of the eyes in the absence of the pep42 peptide, as shown on FIGS. 6b and 6d. Only flies expressing polyQ-hHtt (67aa or 548aa) have normal eyes in the presence of pep42 (FIG. 6c to be compared with FIG. 6e). These results demonstrate the specificity of pep42 action on Huntingtin.

EXAMPLE 5

Inhibiting Properties of Normal Huntingtin and pep42 on Axonal Transport Affected by the Expression of polyQ-hHtt To test the effect of polyQ-hHtt on axonal transport, the fate of vesicles expressing Neuropeptide Y (NPY) labelled with GFP (NPY-GFP) was monitored, either after dissection and fixation of the larvae, or by real-time microscopy in order to monitor vesicular transport in the motor neurons.

a) Fixation of Larvae.

The nervous system of OK6-Gal4 larvae which express vesicles containing NPY-GFP (OK6-Gal4; UAS-NPY-GFP) was dissected and fixed as previously in 3.7% PFA. Incubations with the antibodies and washing are carried out in PBS, 0.3% Triton. Expression of normal Htt$^{548aa}$-0Q has no effect on the vesicles which remain numerous and evenly distributed along the axon. Normal Htt, detected by an anti-Htt HU-4C8 antibody (Chemicon, 1:750), lies along the axon and cannot be detected at the neuromuscular junctions (NMJs). Expression of the hHtt$^{548aa}$-128Q protein leads to the formation of aggregates along the axons and to abnormal accumulation of the protein at the NMJs. We observe a decrease in the total number of vesicles and their accumulation, especially at the aggregates. In all cases, the vesicles reach the NMJs. Addition of pep42 leads to a reduction in the size of the polyQ-hHtt aggregates, non-accumulation of polyQ-hHtt at the NMJs and better distribution of the vesicles along the axons.

b) Real-Time Microscopy.

For this examination, OK6-Gal4; UAS-NPY-GFP larvae were anaesthetised with ether for 2 minutes and positioned with the ventral side upwards between slide and slip cover in polymerised 1% agarose, for direct visualisation using fluorescence microscopy with a 63× objective, to monitor the movement of the vesicles between segments A3 and A4. A film of 100 photographs is taken every 280 ms. For each film, 20 vesicles were analysed with Image J (manual vesicle tracking plugin developed by F. Cordelières, Institut Curie, Orsay, France). Vesicles with an instantaneous speed of less than 0.01 µm/s are defined as having paused. The mean speed is calculated as being the total distance traveled irrespective of the vesicle direction (anterograde or retrograde) divided by the total estimated time during which the vesicle is monitored. While expression of the hHtt$^{548aa}$-128Q protein leads to an increase in the pause time of vesicles and reduces their speed, the presence of pep42 rescues both the vesicle pause time and speed.

c) Larval Locomotion.

Associated with these vesicular problems of OK6-Gal4; UAS-NPY-GFP; UAS-hHtt$^{548aa}$-128Q larvae, 25% lower mobility of the larvae was observed, this mobility being completely rescued in the presence of pep42.

EXAMPLE 6 pep42 Action Mechanism

The protective effect of pep42 can be attributed to either direct interaction with polyQ Huntingtin, or to the fact that pep42 titers factors involved with polyQ htt in the disease. Investigations were therefore conducted to determine whether pep42 could interact with Htt and with which part. Pep42 lies between the 480 and 502 positions of the wild-type protein and can rescue polyQ-hHtt-induced phenotypes expressing different N-ter sizes (67aa, 170aa or 548aa). This suggests that if pep42 acts via direct interaction with Htt, this interaction must take place with the first 67 aa.

This assumption was tested by co-immunoprecipitation experiments using HeLa cells cotransfected by GFP-hHtt$^{171aa}$-136Q or by GFP-P1 (corresponding to the first 98 aa with no polyQ domain), in the presence of Cherry-pep42. A G/A-agarose protein resin binding an anti-GFP was used to immunoprecipitate the GFP-hHtt$^{171aa}$-136Q protein or the GFP-P1 peptide and to co-immunoprecipitate the Cherry-pep42, visualised by an anti-cherry by western blot. These results indicate that pep42 interacts directly with the N-terminal fragment of Huntingtin and that this interaction does not require the presence of the polyQ domain, which explains the specificity of the protective effect of pep42 on Huntington's disease, but not of other polyQ diseases.

The same experiments were successfully repeated using the first 17 amino acids before the polyQ domain of the human Htt protein.

EXAMPLE 7

Diffusion Property of Pep42-TAT Fusion Peptide and Conservation of Protective Activity Diffusion in HeLa Cells (FIG. 7a)

The TAMRA (Tetramethylrhodamine 5-Carboxamido-(6-Azidohexanyl) fluorescent marker is coupled with pep42-TAT to obtain the TAMRA-pep42-TAT fusion peptide. TAMRA-pep42-TAT is added to a HeLa cell culture medium. The fluorescence of these peptides is then visualised in fluorescence microscopy (FIG. 7a) which is superimposed with the same view in phase contrast microscopy (FIG. 7b). FIG. 7b clearly shows that the fluorescence is well delimited inside the cells and that the fusion peptide (TAMRA-PEP42-TAT) has diffused from the culture medium to penetrate into the cell cytoplasm.

Activity in HeLa Cells (FIG. 7c)

HeLa cells are transfected with:

1—GFP-polyQ-hHtt (Q136),

2—GFP-polyQ-hHtt co-transfected with a vector expressing Pep42-TAT, or

3—GFP-polyQ-hHtt in the presence of an increasing quantity of Pep42-TAT synthetic peptide added to the culture medium.

FIG. 7c corresponds to the aggregate percentage identified by the GFP signal related to the polyQ-hHtt chain, in the presence of an increasing quantity of fusion peptide. We see that the quantity of GFP in the cells decreases significantly.

These experiments demonstrate that the protective activity of the fusion peptide is conserved.

Figure 8A:
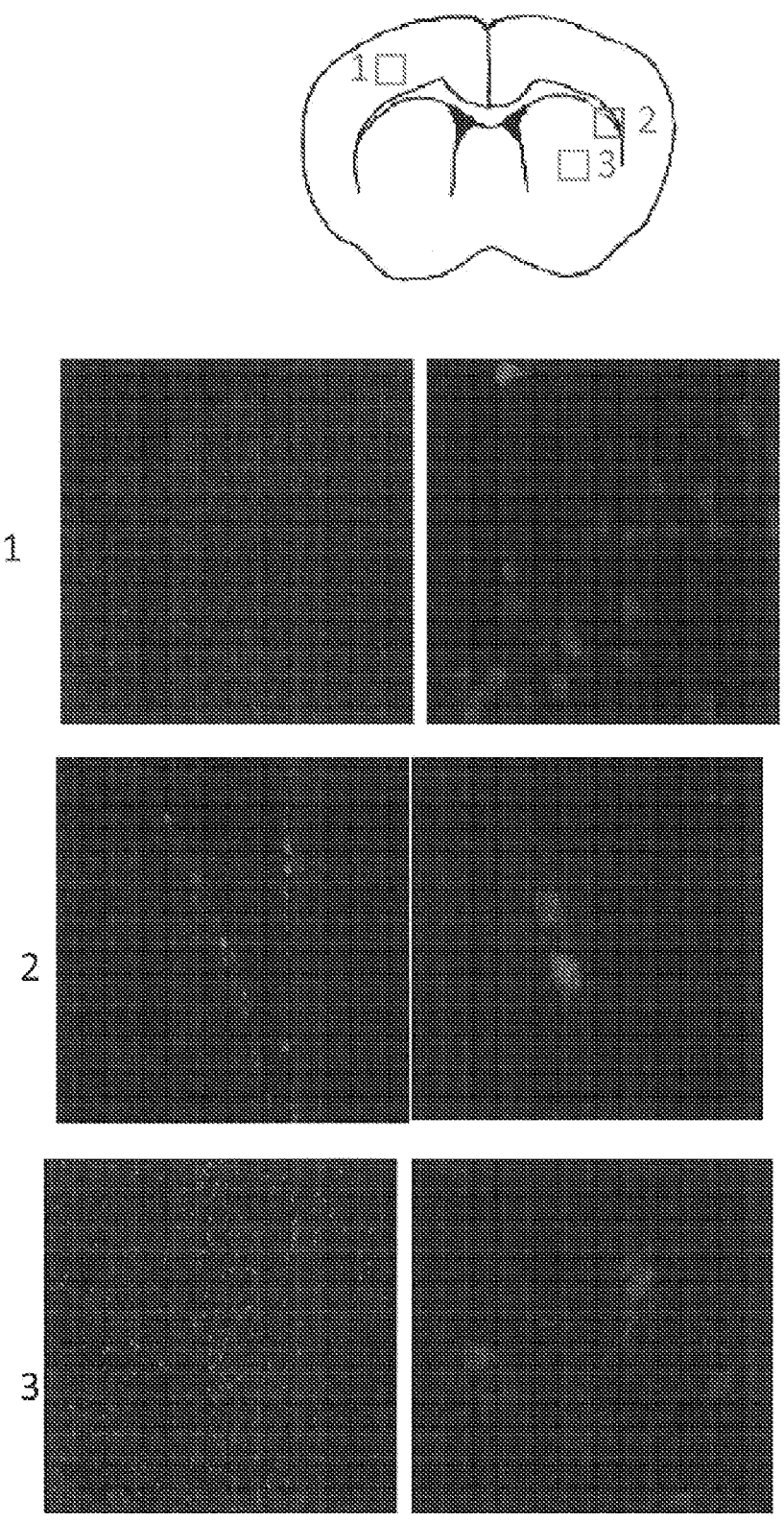

Diffusion in Mouse Brain (FIG. 8a)

An intracerebroventricular (ICV) injection of 5 μg of TAMRA-Pep-42-TAT is carried out at a rate of 1 μg/min, followed by analysis of brain sections either 6 hours after the injection (FIG. 8a), or 24 hours after the injection.

FIG. 8a shows the images at two different magnifications of the following sections:

1—Left cortex section,
2—Right ventricle section, and
3—Sub-cortical section (striatum).

Intra-cellular marking represented by a light grey colour in the figure is observed on all three sections.

Figure 8B:
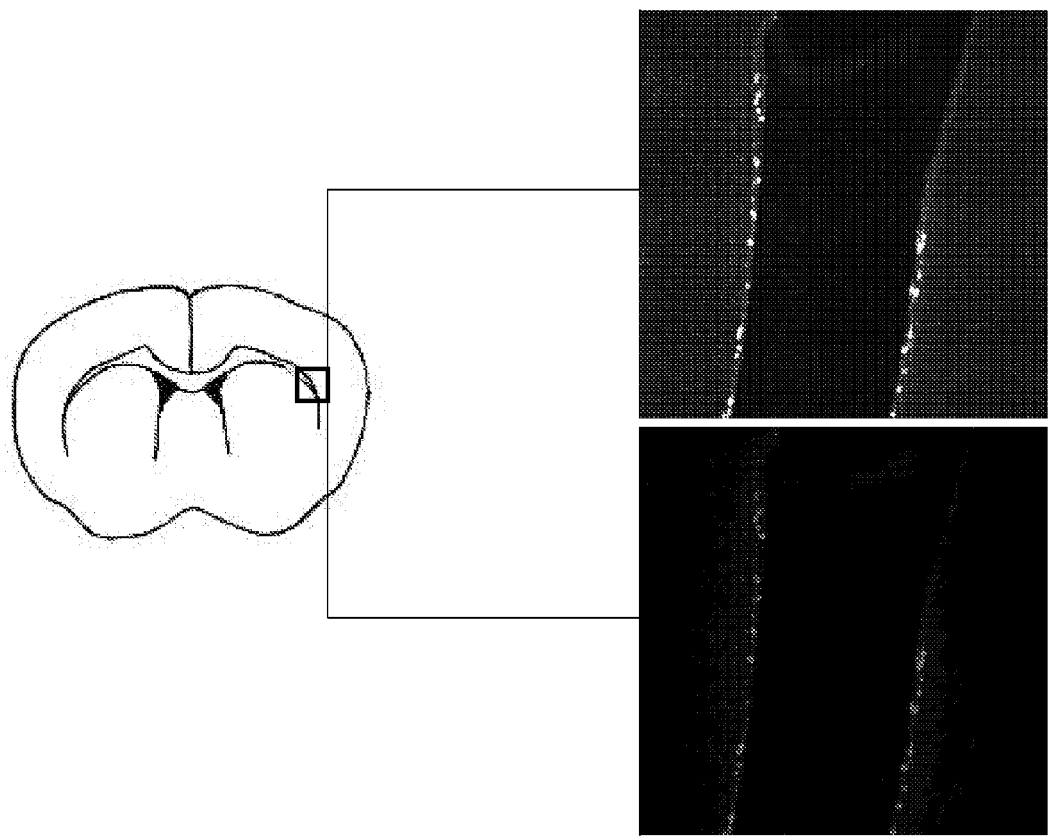

Stability at 24 h (FIG. 8b)

The fluorescence is analysed after 24 hours and we examine the results shown on FIG. 8b which demonstrates the presence of the fusion peptide near the ventricles and therefore its stability after 24 hours.

The invention claimed is:

1. A fusion protein, comprising:
   (i) a peptide of less than 100 amino acids comprising:
      a first amino acid sequence comprising AASSG (SEQ ID NO: 1), and
      a second amino acid sequence comprising XAGXDXXTEXPXS (SEQ ID NO: 2), wherein X designates any amino acid; and
   (ii) a protein transduction domain (PTD).

2. The fusion protein according to claim 1, wherein the second amino acid sequence is SAGHDIITEQPRS (SEQ ID NO: 3) or NAGEDAPTEAPSS (SEQ ID NO: 6).

3. The fusion protein according to claim 1, wherein said peptide comprises SEQ ID NO: 4 or SEQ ID NO: 5.

4. The fusion protein according to claim 1, wherein the protein transduction domain is Transacting Activator of Transcription (TAT) peptide or Penetratin peptide.

5. The fusion protein according to claim 4, wherein the protein transduction domain comprises SEQ ID NO: 11.

6. The fusion protein according to claim 4, wherein the protein transduction domain comprises SEQ ID NO: 12.

7. The fusion protein according to claim 4, wherein the fusion protein consists of the amino acid sequence SEQ ID NO: 13.

8. A polynucleotide coding for the fusion protein according to claim 1.

9. An expression vector containing the polynucleotide according to claim 8.

10. The vector according to claim 9, the vector being a virus type expression vector.

11. A host cell containing the expression vector according to claim 9.

12. A pharmaceutical composition comprising
   a fusion protein comprising:
      (i) a peptide of less than 200 amino acids comprising:
         a first amino acid sequence comprising AASSG (SEQ ID NO: 1), and
         a second amino acid sequence comprising XAGXDXXTEXPXS (SEQ ID NO: 2), wherein X designates any amino acid, and
      (ii) a protein transduction domain (PTD), or
         a polynucleotide coding for said fusion protein, or
         an expression vector containing said polynucleotide,
   in association with a pharmaceutically acceptable carrier.

13. The pharmaceutical composition according to claim 12, wherein said peptide comprises SEQ ID NO: 4 or SEQ ID NO: 5.

14. The pharmaceutical composition according to claim 12, wherein the second amino acid sequence consists of the sequence selected from the group consisting of SAGHDIITEQPRS (SEQ ID NO: 3) and NAGEDAPTEAPSS (SEQ ID NO: 6).

15. The pharmaceutical composition according to claim 12, wherein the fusion protein consists of the amino acid sequence SEQ ID NO: 13.

16. The pharmaceutical composition according to claim 12, wherein the protein transduction domain is selected from the group consisting of Transacting Activator of Transcription (TAT) peptide and Penetratin peptide.

17. The pharmaceutical composition according to claim 16, wherein the TAT peptide consists of the amino acid sequence SEQ ID NO: 11.

18. The pharmaceutical composition according to claim 16, wherein the Penetratin peptide consists of the amino acid sequence SEQ ID NO: 12.

19. A method for treating Huntington's disease in a patient in need thereof, said method comprising administering to the patient an effective amount of
   an isolated peptide of less than 200 amino acids comprising:
      a first amino acid sequence AASSG (SEQ ID NO: 1), and
      a second sequence XAGXDXXTEXPXS (SEQ ID NO: 2), wherein X designates any amino acid,
   or
      a fusion protein comprising
         (i) a peptide of less than 200 amino acids comprising:
            a first amino acid sequence AASSG (SEQ ID NO: 1), and
            a second amino acid sequence XAGXDXXTEXPXS (SEQ ID NO: 2), wherein X designates any amino acid, and
         (ii) a protein transduction domain (PTD), or
            a polynucleotide coding for said isolated peptide or said fusion protein, or
            an expression vector containing said polynucleotide.

20. The method for treating Huntington's disease according to claim 19, wherein said isolated peptide comprises SEQ ID NO: 4 or SEQ ID NO: 5.

21. The method for treating Huntington's disease according to claim 19, wherein the fusion protein consists of the amino acid sequence SEQ ID NO: 13.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: extracted from human Huntingtin

<400> SEQUENCE: 1

Ala Ala Ser Ser Gly
1               5

<210> SEQ ID NO 2
<211> LENGTH: 13
<212> TYPE: PRT
<213> ORGANISM: Artificial Sequence
<220> FEATURE:
<223> OTHER INFORMATION: derived from human Huntingtin
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 2

Xaa Ala Gly Xaa Asp Xaa Xaa Thr Glu Xaa Pro Xaa Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: extracted from human Huntingtin

<400> SEQUENCE: 3

Ser Ala Gly His Asp Ile Ile Thr Glu Gln Pro Arg Ser
1               5                   10
```

<210> SEQ ID NO 4
<211> LENGTH: 23
<212> TYPE: PRT
<213> ORGANISM: Artificial Sequence
<220> FEATURE:
<223> OTHER INFORMATION: Pep42

<400> SEQUENCE: 4

Ala Ala Ser Ser Gly Val Ser Thr Pro Gly Ser Ala Gly His Asp Ile
1               5                   10                  15

Ile Thr Glu Gln Pro Arg Ser
            20

<210> SEQ ID NO 5
<211> LENGTH: 166
<212> TYPE: PRT
<213> ORGANISM: Artificial Sequence
<220> FEATURE:
<223> OTHER INFORMATION: Pep4

<400> SEQUENCE: 5

Gln Gln Leu Phe Arg Thr Pro Pro Glu Leu Leu Gln Thr Leu Thr
1               5                   10                  15

Ala Val Gly Gly Ile Gly Gln Leu Thr Ala Ala Lys Glu Glu Ser Gly
                20                  25                  30

Gly Arg Ser Arg Ser Gly Ser Ile Val Glu Leu Ile Ala Gly Gly Gly
            35                  40                  45

Ser Ser Cys Ser Pro Val Leu Ser Arg Lys Gln Lys Gly Lys Val Leu
        50                  55                  60

Leu Gly Glu Glu Glu Ala Leu Glu Asp Asp Ser Glu Ser Arg Ser Asp
65                  70                  75                  80

Val Ser Ser Ser Ala Leu Thr Ala Ser Val Lys Asp Glu Ile Ser Gly
                85                  90                  95

Glu Leu Ala Ala Ser Ser Gly Val Ser Thr Pro Gly Ser Ala Gly His
                100                 105                 110

Asp Ile Ile Thr Glu Gln Pro Arg Ser Gln His Thr Leu Gln Ala Asp
            115                 120                 125

Ser Val Asp Leu Ala Ser Cys Asp Leu Thr Ser Ser Ala Thr Asp Gly
        130                 135                 140

Asp Glu Glu Asp Ile Leu Ser His Ser Ser Ser Gln Val Ser Ala Val
145                 150                 155                 160

Pro Ser Asp Pro Ala Met
                165

<210> SEQ ID NO 6
<211> LENGTH: 13
<212> TYPE: PRT
<213> ORGANISM: Artificial Sequence
<220> FEATURE:
<223> OTHER INFORMATION: derived from Drosophila Huntingtin

<400> SEQUENCE: 6

Asn Ala Gly Glu Asp Ala Pro Thr Glu Ala Pro Ser Ser
1               5                   10

<210> SEQ ID NO 7
<211> LENGTH: 69
<212> TYPE: DNA
<213> ORGANISM: Artificial Sequence
<220> FEATURE:
<223> OTHER INFORMATION: derived from human Huntingtin

<400> SEQUENCE: 7

```
gctgcttctt cagggggtttc cactccaggg tcagcaggtc atgacatcat cacagaacag    60
ccacggtca                                                             69
```

<210> SEQ ID NO 8
<211> LENGTH: 498
<212> TYPE: DNA
<213> ORGANISM: Artificial Sequence
<220> FEATURE:
<223> OTHER INFORMATION: extracted from human Huntingtin

<400> SEQUENCE: 8

```
cagcagctct tcagaacgcc tccacccgag cttctgcaaa ccctgactgc agtcgggggc     60
attgggcagc tcaccgctgc taaggaggag tctggtggcc gaagccgtag tgggagtatt   120
gtggaactta tagctggagg gggttcctca tgcagccctg tcctttcaag aaaacaaaaa   180
ggcaaagtgc tcttaggaga agaagaagcc ttggaggatg actctgaatc gagatcggat   240
gtcagcagct ctgccttaac agcctcagtg aaggatgaga tcagtggaga gctggctgct   300
tcttcagggg tttccactcc agggtcagca ggtcatgaca tcatcacaga acagccacgg   360
tcacagcaca cactgcaggc ggactcagtg atctggcca gctgtgactt gacaagctct   420
gccactgatg gggatgagga ggatatcttg agccacagct ccagccaggt cagcgccgtc   480
ccatctgacc ctgccatg                                                 498
```

<210> SEQ ID NO 9
<211> LENGTH: 620
<212> TYPE: PRT
<213> ORGANISM: Drosophila

<400> SEQUENCE: 9

```
Met Asp Lys Ser Arg Ser Ser Ala Tyr Asp Lys Phe Val Gly Phe Val
1               5                   10                  15

Glu Gln Leu Arg Asn Thr Glu Cys Ser Gln Lys Gln Lys Ile Thr Cys
            20                  25                  30

Phe Gln Gln Ile Ala Glu Cys Ile Met Ser Pro Ser Leu Ala Gly His
        35                  40                  45

Ile Asn Tyr Ala Ala His Cys Gly Thr Ala Thr Asn Val Leu Leu Leu
    50                  55                  60

Phe Cys Glu Asp Val Asp Ser Val Val Arg Met Ser Ala Glu Glu Asn
65                  70                  75                  80

Leu Asn Lys Ile Leu Arg Ser Leu Glu Lys Thr Arg Val Ser Arg Ile
                85                  90                  95

Leu Met Asp Leu Tyr Gly Glu Ile Lys Arg Asn Gly Asn Gln Arg Ser
            100                 105                 110

Leu Arg Ile Cys Leu Asn Leu Phe Ser Tyr Tyr Ala Pro Gln Ile Lys
        115                 120                 125

Glu Lys His Ile Lys Trp Tyr Ala Val Arg Leu Leu Gln Cys Met Thr
    130                 135                 140

Thr Ile Ser Gln Arg Lys Glu Thr Leu Leu Gln Glu Thr Leu Cys Asp
145                 150                 155                 160

Phe Val Lys His Phe Ser Arg His Ile Gln Gln Gly Leu Ser Asp Ser
                165                 170                 175

Glu Ser Cys Lys Leu Phe Glu Thr Phe Leu Asp Gln Ile Ser Ser Asp
            180                 185                 190
```

```
Cys Ala Val Lys Arg Arg Cys Ser Ala Gln Asn Cys Met Ser Leu Ile
            195                 200                 205

Glu Asn Ala Arg Asn Arg Ser Leu Met Ala Arg His Gly Val Asn Lys
        210                 215                 220

Val Met Glu Leu Leu Leu Thr Asp Gln Gln Ala Asn Ser Val Leu Gly
225                 230                 235                 240

Ala Leu Gly Leu Leu Arg Leu Leu Pro Gln Leu Ile Arg Gly Tyr
                245                 250                 255

Pro Gly Asp Ser His Glu Asp Ser Glu Ser Leu Ala Gly Lys Lys Gln
                260                 265                 270

Gln Gln Gln Gln Thr Thr Thr Ser Asp Cys Arg Gln Ile Ile Glu Ile
                275                 280                 285

Tyr Asp Tyr Cys Leu His Leu Leu Ser Thr Gln His Thr Ala Asn His
        290                 295                 300

Ala Ile Ile Asn Ala Thr Leu Glu Val Ile Asn Gly Ile Leu Gln Ala
305                 310                 315                 320

Val Asp Ala Ala Ser Asp Gly Gln Cys Ser Gln Ser Leu Gly Gln Ser
                325                 330                 335

Leu Arg Gln Leu Leu Cys Asn Gln Gln Leu Gln His Asn Glu Tyr Leu
                340                 345                 350

Arg Arg Arg Lys Ser Leu Lys Asn Gln Ile Phe Gln Leu Lys Asn Tyr
                355                 360                 365

Glu Val Ala Thr Ser Gln His Gln Leu Glu Asp Glu Asp Glu Asn Glu
                370                 375                 380

Asp Val Asp Glu Leu Val Val Gly Ala Thr Ala Met Gln Met Lys Lys
385                 390                 395                 400

Asn Ser Asn Ala Lys Leu Gln Gln Ala Lys Cys Arg Glu Gln Gln Gln
                405                 410                 415

His Gln His Gln Gln Gln Leu Glu Val Asp Asn Ser Ser Leu Gly Ile
                420                 425                 430

Asn Ala Gly Glu Asp Ala Pro Thr Glu Ala Pro Ser Ser Val Ala Asp
                435                 440                 445

Glu Gly Gly Glu Pro Glu Ser Thr Lys Leu Arg Cys His Ile Arg Asn
450                 455                 460

Ala Ala Arg Ser Ile Ser Glu Cys Val Ala Ser Asp Glu Asp Lys Gln
465                 470                 475                 480

Gly Gln Gly His Arg Gln Arg Asp Glu Asp Gly Val Val Ala
                485                 490                 495

Glu Asp Asp Asp Asp Asp Asp Asp Asp Asp Asp Asp Asp Met
                500                 505                 510

Glu Leu Leu Ser Ala Glu Cys Asp Asp Phe Thr Thr Leu Ser Gln Leu
        515                 520                 525

Asn Gln Gln Gln Ala Leu Ser Ala Ala Leu Lys Leu Pro Thr Thr
530                 535                 540

Thr Ala Ala Ser Ser Gly Gly Ala Ala Thr Ser Gln Asp Asp Lys Leu
545                 550                 555                 560

Ile Asp Val Asp Ala Asp Val Gly Gly Leu Pro Lys Pro Gln His Gln
                565                 570                 575

Ser Ser Leu Gln Asn Leu Leu Ala Gly Ser Asp Lys Ser Gln His
                580                 585                 590

Leu Ser Asp Ile Asp Asn Glu Ser Phe Asn Ser Ile Asp Phe Asp Ala
                595                 600                 605

Glu Ile Thr Ile Ala Gly Ser Lys Glu Gln Gln Gln
```

-continued

<210> SEQ ID NO 10
<211> LENGTH: 570
<212> TYPE: PRT
<213> ORGANISM: Homo sapiens

<400> SEQUENCE: 10

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Pro Pro Pro Pro Pro Pro Pro Pro Pro Pro Pro
        35                  40                  45

Pro Gln Leu Pro Gln Pro Pro Pro Gln Ala Gln Pro Leu Leu Pro Gln
    50                  55                  60

Pro Gln Pro Pro Pro Pro Pro Pro Pro Pro Gly Pro Ala Val
65                  70                  75                  80

Ala Glu Glu Pro Leu His Arg Pro Lys Lys Glu Leu Ser Ala Thr Lys
                85                  90                  95

Lys Asp Arg Val Asn His Cys Leu Thr Ile Cys Glu Asn Ile Val Ala
            100                 105                 110

Gln Ser Val Arg Asn Ser Pro Glu Phe Gln Lys Leu Leu Gly Ile Ala
        115                 120                 125

Met Glu Leu Phe Leu Leu Cys Ser Asp Asp Ala Glu Ser Asp Val Arg
    130                 135                 140

Met Val Ala Asp Glu Cys Leu Asn Lys Val Ile Lys Ala Leu Met Asp
145                 150                 155                 160

Ser Asn Leu Pro Arg Leu Gln Leu Glu Leu Tyr Lys Glu Ile Lys Lys
                165                 170                 175

Asn Gly Ala Pro Arg Ser Leu Arg Ala Ala Leu Trp Arg Phe Ala Glu
            180                 185                 190

Leu Ala His Leu Val Arg Pro Gln Lys Cys Arg Pro Tyr Leu Val Asn
        195                 200                 205

Leu Leu Pro Cys Leu Thr Arg Thr Ser Lys Arg Pro Glu Glu Ser Val
    210                 215                 220

Gln Glu Thr Leu Ala Ala Ala Val Pro Lys Ile Met Ala Ser Phe Gly
225                 230                 235                 240

Asn Phe Ala Asn Asp Asn Glu Ile Lys Val Leu Leu Lys Ala Phe Ile
                245                 250                 255

Ala Asn Leu Lys Ser Ser Pro Thr Ile Arg Arg Thr Ala Ala Gly
            260                 265                 270

Ser Ala Val Ser Ile Cys Gln His Ser Arg Arg Thr Gln Tyr Phe Tyr
        275                 280                 285

Ser Trp Leu Leu Asn Val Leu Leu Gly Leu Leu Val Pro Val Glu Asp
    290                 295                 300

Glu His Ser Thr Leu Leu Ile Leu Gly Val Leu Leu Thr Leu Arg Tyr
305                 310                 315                 320

Leu Val Pro Leu Leu Gln Gln Gln Val Lys Asp Thr Ser Leu Lys Gly
                325                 330                 335

Ser Phe Gly Val Thr Arg Lys Glu Met Glu Val Ser Pro Ser Ala Glu
            340                 345                 350

Gln Leu Val Gln Val Tyr Glu Leu Thr Leu His His Thr Gln His Gln
        355                 360                 365

```
Asp His Asn Val Val Thr Gly Ala Leu Glu Leu Leu Gln Gln Leu Phe
    370                 375                 380

Arg Thr Pro Pro Glu Leu Leu Gln Thr Leu Thr Ala Val Gly Gly
385                 390                 395                 400

Ile Gly Gln Leu Thr Ala Ala Lys Glu Glu Ser Gly Gly Arg Ser Arg
                405                 410                 415

Ser Gly Ser Ile Val Glu Leu Ile Ala Gly Gly Ser Ser Cys Ser
                420                 425                 430

Pro Val Leu Ser Arg Lys Gln Lys Gly Lys Val Leu Leu Gly Glu Glu
                435                 440                 445

Glu Ala Leu Glu Asp Asp Ser Glu Ser Arg Ser Asp Val Ser Ser Ser
450                 455                 460

Ala Leu Thr Ala Ser Val Lys Asp Glu Ile Ser Gly Glu Leu Ala Ala
465                 470                 475                 480

Ser Ser Gly Val Ser Thr Pro Gly Ser Ala Gly His Asp Ile Ile Thr
                485                 490                 495

Glu Gln Pro Arg Ser Gln His Thr Leu Gln Ala Asp Ser Val Asp Leu
                500                 505                 510

Ala Ser Cys Asp Leu Thr Ser Ser Ala Thr Asp Gly Asp Glu Glu Asp
                515                 520                 525

Ile Leu Ser His Ser Ser Ser Gln Val Ser Ala Val Pro Ser Asp Pro
530                 535                 540

Ala Met Asp Leu Asn Asp Gly Thr Gln Ala Ser Ser Pro Ile Ser Asp
545                 550                 555                 560

Ser Ser Gln Thr Thr Thr Glu Gly Pro Asp
                565                 570

<210> SEQ ID NO 11
<211> LENGTH: 11
<212> TYPE: PRT
<213> ORGANISM: Artificial Sequence
<220> FEATURE:
<223> OTHER INFORMATION: Protein Transductor Domain

<400> SEQUENCE: 11

Tyr Gly Arg Lys Lys Arg Arg Gln Arg Arg
1               5                   10

<210> SEQ ID NO 12
<211> LENGTH: 16
<212> TYPE: PRT
<213> ORGANISM: Artificial Sequence
<220> FEATURE:
<223> OTHER INFORMATION: extracted from antennapedia protein

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 36
<212> TYPE: PRT
<213> ORGANISM: Artificial Sequence
<220> FEATURE:
<223> OTHER INFORMATION: Pep42-TAT
```

```
<400> SEQUENCE: 13

Ala Ala Ser Ser Gly Val Ser Thr Pro Gly Ser Ala Gly His Asp Ile
1               5                   10                  15

Ile Thr Glu Gln Pro Arg Ser Gly Gly Tyr Gly Arg Lys Lys Arg Arg
            20                  25                  30

Gln Arg Arg
        35
```